(12) United States Patent
Brett

(10) Patent No.: US 6,673,063 B2
(45) Date of Patent: Jan. 6, 2004

(54) EPIDURAL THERMAL POSTERIOR ANNULOPLASTY

(75) Inventor: Darrell C. Brett, Portland, OR (US)

(73) Assignee: Expanding Concepts, LLC., Portland, OR (US)

( * ) Notice: Subject to any disclaimer, the term of this patent is extended or adjusted under 35 U.S.C. 154(b) by 243 days.

(21) Appl. No.: 09/832,642

(22) Filed: Apr. 10, 2001

(65) Prior Publication Data

US 2003/0158591 A1 Aug. 21, 2003

Related U.S. Application Data

(60) Provisional application No. 60/238,803, filed on Oct. 6, 2000.

(51) Int. Cl.⁷ .......................... A61B 18/18; A61B 18/20
(52) U.S. Cl. ........................ 606/10; 606/13; 606/16; 606/18; 606/41; 606/46; 607/88; 607/89; 607/999; 607/100; 607/101
(58) Field of Search ................. 606/3–7, 10–17, 606/40–52; 607/88, 89, 91–103, 108

(56) References Cited

U.S. PATENT DOCUMENTS

| | | | |
|---|---|---|---|
| 5,203,353 A | * | 4/1993 | Easley et al. |
| 5,334,193 A | | 8/1994 | Nardella |
| 5,348,554 A | | 9/1994 | Imran et al. |
| 5,374,265 A | | 12/1994 | Sand |
| 5,433,739 A | | 7/1995 | Sluijter et al. |
| 5,458,596 A | | 10/1995 | Lax et al. |
| 5,484,432 A | | 1/1996 | Sand |
| 5,569,242 A | | 10/1996 | Lax et al. |
| 5,571,147 A | | 11/1996 | Sluijter et al. |
| 5,865,833 A | | 2/1999 | Daikuzono |
| 5,954,716 A | | 9/1999 | Sharkey et al. |
| 6,007,533 A | | 12/1999 | Casscells et al. |
| 6,007,570 A | | 12/1999 | Sharkey et al. |
| 6,071,280 A | * | 6/2000 | Edwards et al. |
| 6,073,051 A | | 6/2000 | Sharkey et al. |
| 6,095,149 A | | 8/2000 | Sharkey et al. |
| 6,122,549 A | | 9/2000 | Sharkey et al. |
| 6,264,650 B1 | | 7/2001 | Hovda et al. |
| 6,264,651 B1 | | 7/2001 | Underwood et al. |
| 6,277,112 B1 | | 8/2001 | Underwood et al. |
| 6,277,116 B1 | | 8/2001 | Utely et al. |
| 6,283,960 B1 | | 9/2001 | Ashley |
| 6,283,961 B1 | | 9/2001 | Underwood et al. |
| 6,482,204 B1 | | 11/2002 | Lax et al. |

FOREIGN PATENT DOCUMENTS

WO    WO 01/26570 A1    4/2001

* cited by examiner

*Primary Examiner*—David M. Shay
(74) *Attorney, Agent, or Firm*—Karen Dana Oster

(57) ABSTRACT

An apparatus for thermally treating intervertebral discs includes an energy application head having an energy application region and a tissue protecting region. A control member operationally connected to the energy application head preferably controls the energy application head during treatment. The present invention also includes a method for thermally treating an intervertebral disc.

30 Claims, 7 Drawing Sheets

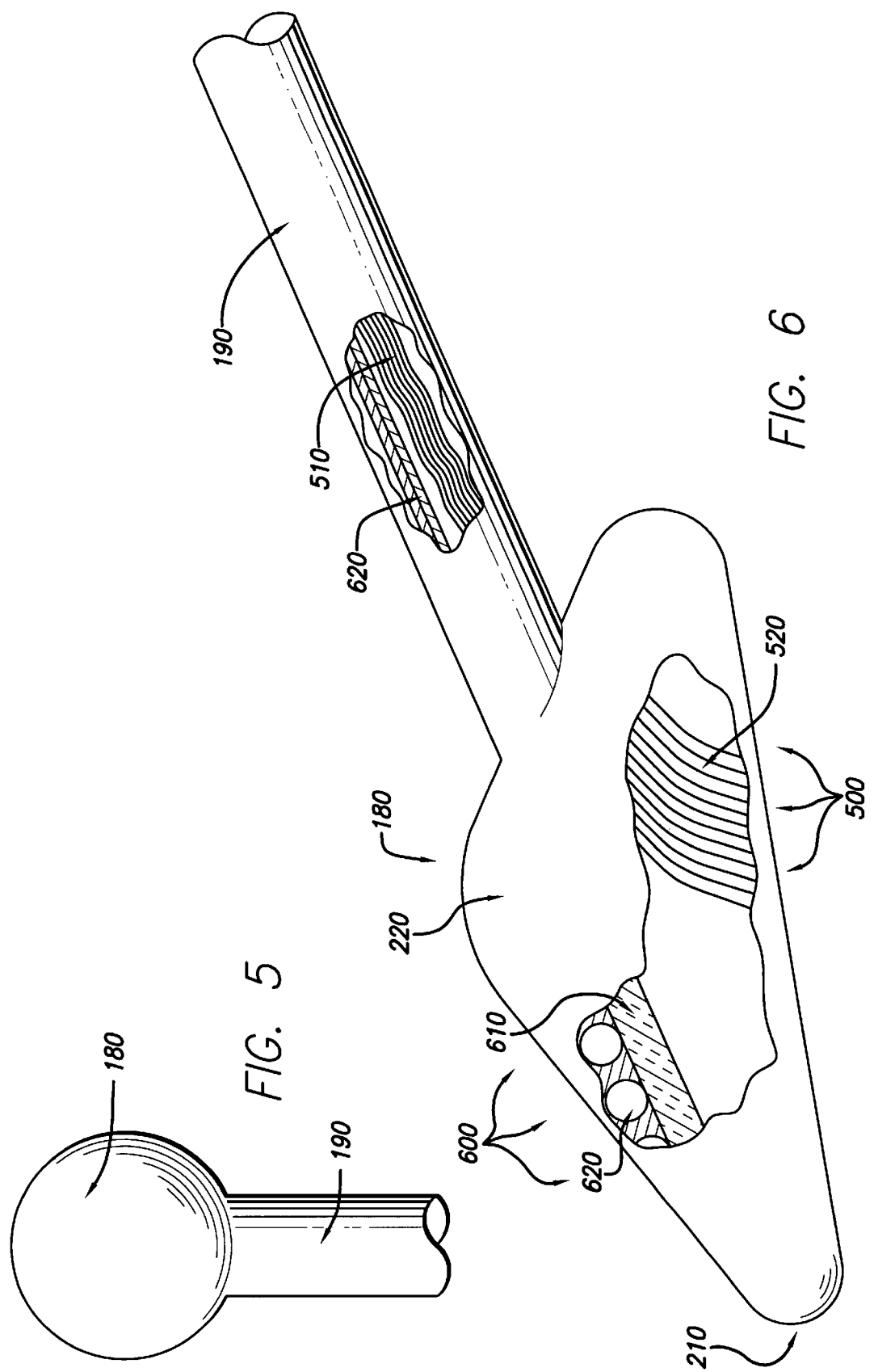

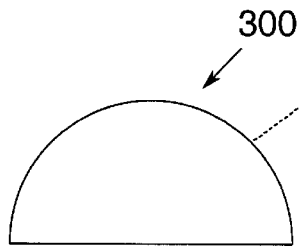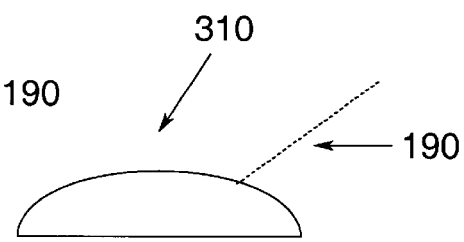
FIG. 7    FIG. 8
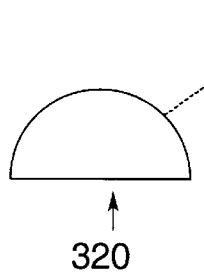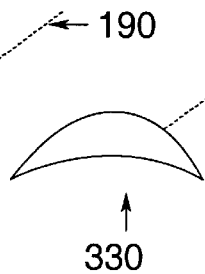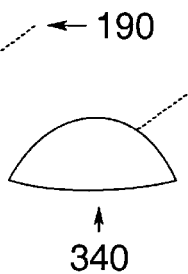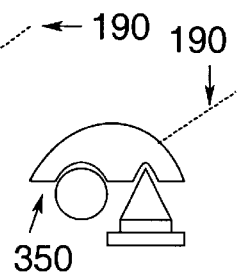
FIG. 9    FIG. 10    FIG. 11    FIG. 12
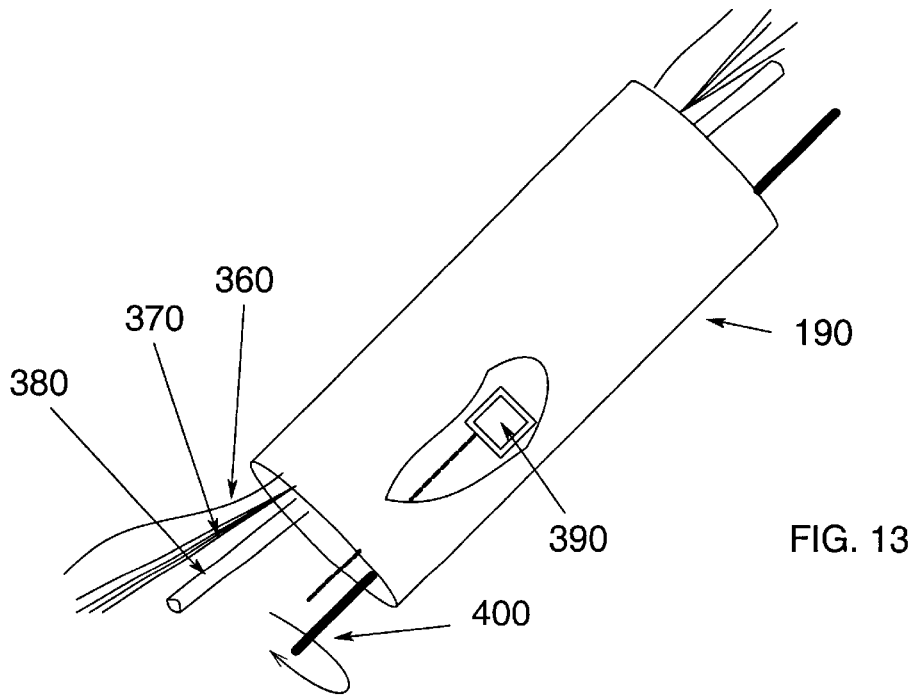
FIG. 13

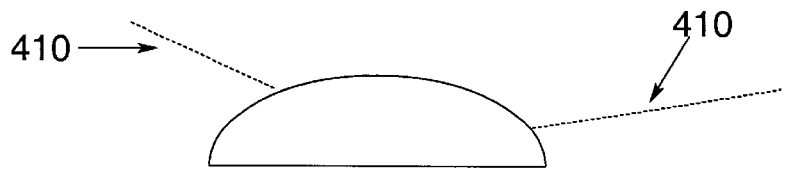
FIG. 14
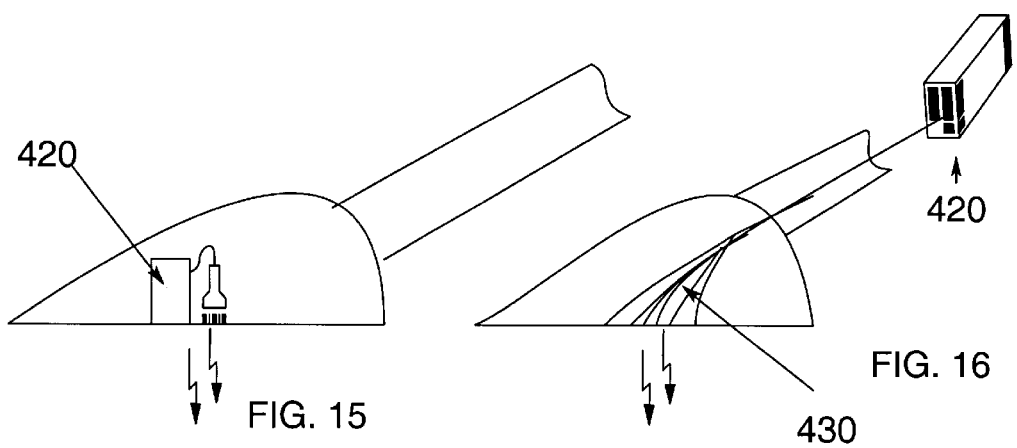
FIG. 15
FIG. 16
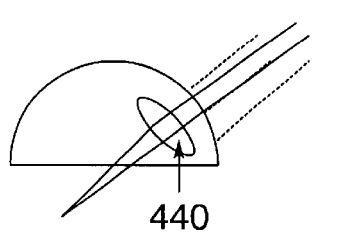
FIG. 17
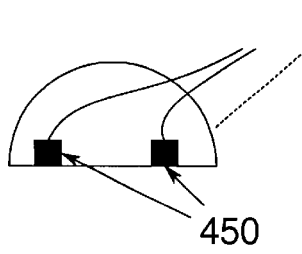
FIG. 18
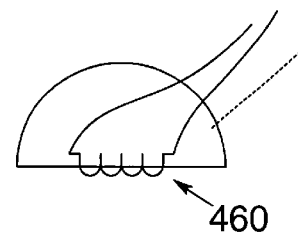
FIG. 19
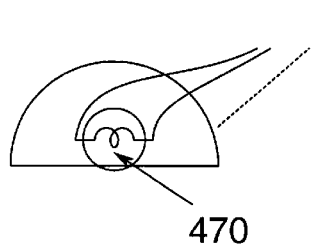
FIG. 20
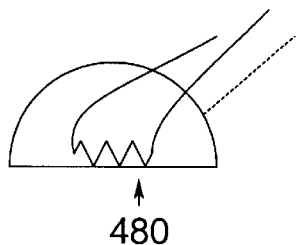
FIG. 21
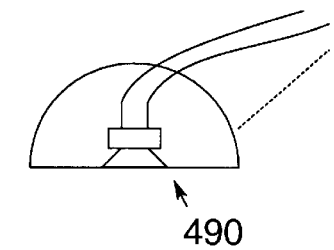
FIG. 22

EPIDURAL THERMAL POSTERIOR ANNULOPLASTY

This application claims the benefit of Provisional application No. 60/238,803 filed Oct. 6, 2000.

BACKGROUND OF THE INVENTION

The present invention is directed to a treatment for injured or degenerated intervertebral discs. Specifically, the present invention is a method and apparatus for strengthening an injured or degenerated intervertebral disc and relieving pain. The treatment may allow a spine surgeon to avoid a discectomy and removal of the nucleus pulposus during laminectomy operations and may reduce postoperative discogenic pain.

As shown in FIG. 1, each intervertebral disc 10 is a cushionlike pad with top and bottom endplates adjoining the bone surfaces on each adjacent vertebral body 20. As shown in FIG. 2, each disc has an inner sphere, the nucleus pulposus 30, which acts as a cushion for compressive stress. Around the nucleus pulposus is an outer collar of approximately 12 concentric rings, the annulus fibrosis 40, which limits the expansion of the nucleus pulposus when the spine is compressed. The rings of the annulus fibrosis also bind the successive vertebrae together, resist torsion of the spine, and assist the nucleus pulposus in absorbing compressive forces.

The grains of collagen fibers in adjacent rings of the annulus fibrosis 40 run in different directions so that the grains cross like an X. This arrangement of the collagen layers allows the spine to withstand twisting, shear forces.

FIG. 2 shows an exemplary injury to an intervertebral disc. A herniated or prolapsed disc is commonly called a "slipped disc." Severe or sudden trauma to the spine or nontraumatic pathology such as degenerative spine disease may cause a bulge, rupture, degeneration, or other area of injury ("injury") 50 in one or more intervertebral discs. The annulus fibrosis 40 is thinnest posteriorly in the general direction of the spinous process 60, so the nucleus pulposus 30 usually herniates in that direction. The injury usually proceeds posterolaterally instead of directly posteriorly because the posterior longitudinal ligament strengthens the annulus fibrosis at the posterior sagittal midline of the annulus. The terms "posterior" and "posteriorly" mean the general posterior and posterolateral aspects of the disc as distinguished from the anterior aspects of the disc. The posterior aspect of the annulus fibrosis is also the location of vulnerable nerve tissues, including but not limited to the cauda equina 70 and spinal nerve roots 80.

A posterior injury of the nucleus pulposus often impinges on the spinal nerve roots 80 exiting the spinal canal 90. The resulting pressure on these nerve roots often leads to pain and/or numbness in the lower extremities. Injured intervertebral discs are treated with bed rest, physical therapy, modified activities, and painkillers over time. If these treatments are ineffective, the injured and usually protruding disc is often surgically removed.

Current treatments offer only limited success in avoiding surgical removal of injured intervertebral discs that do not heal themselves over time. A few treatments are adopted for use on an intervertebral disc from broad methods to shrink collagen in various other parts of the body. Several treatments attempt to reduce discogenic pain.

Several exemplary prior art references disclose using heat to shrink collagen. U.S. Pat. Nos. 5,374,265 and 5,484,432 to Sand (the "Sand references") are directed to methods for shrinking collagen with an infrared laser. The collagen shrinkage in the Sand references is generally accomplished in an ophthalmological context. Laser light that is optimally absorbed by collagen tissue is applied to a corneal stoma resulting in collagen shrinkage and reshaping of the cornea for vision correction. Although the Sand method generally applies to shrinkage of collagen, it only contemplates applying relatively small amounts of energy to delicate eye tissue. No provision is made for protecting vulnerable tissue near collagen in other parts of the body. The amount of energy needed to shrink collagen in synovial joints or the spine is greater than the amount needed for eye tissue and may damage vulnerable tissue near the collagen being treated.

U.S. Pat. Nos. 5,458,596 and 5,569,242 to Lax et al. (the "Lax references") are directed to broad methods and apparatuses for controlled contraction of soft tissue. The Lax references disclose the application of radio frequency energy through an electrode to tissue containing collagen. Such an application of energy as envisioned by the Lax references to an intervertebral disc would damage vulnerable tissues near the application site. The Lax references do not disclose the use of energy other than radio frequency. The shape of the Lax electrode is not designed for use on the spine. Also, because the Lax electrode is a general applicator, it does not protect vulnerable tissues during application of energy and therefore would not be suitable for applications involving the spine.

U.S. Pat. No. 5,954,716 to Sharkey et al. (the "Sharkey '716 reference") is directed to a method and device for modifying the length of a ligament. In the Sharkey '716 reference, radio frequency energy is applied to one ligament in a set of opposing ligaments. Only radio frequency energy is disclosed. The radio frequency energy shrinks one ligament, restoring equal length and a balance of function to the set of opposing ligaments. Although the Sharkey '716 treatment uses radio frequency energy to shrink a ligament, it would not work on an intervertebral disc because an intervertebral disc is surrounded by vulnerable tissues. Because intervertebral discs lie close to the spinal canal and spinal nerve roots, application without thermal protection of radio frequency energy suitable for shrinking a ligament might harm vulnerable nerve tissues.

Heating an intervertebral disc for relief of discogenic pain is disclosed in U.S. Pat. Nos. 5,433,739 and 5,571,147 to Sluijter et al. (the "Sluijter references"). In the Sluijter references, probes are inserted into an intervertebral disc by puncturing the annulus fibrosis. Radio frequency or direct current energy is delivered through probes to heat the nucleus pulposus of a disc to approximately 60° C. to 70° C. The heat travels to the outer perimeter of the disc being treated so that the entire disc is heated. The applied heat relieves back pain by denervating fine nerve endings in the disc. Although the probes of the Sluijter references may relieve back pain, the Sluijter probes invade the disc and are not intended to shrink collagen or repair a bulging, ruptured, or injured intervertebral disc. Since the entire disc is heated to approximately 60° C. to 70° C., the heat may harm vulnerable tissues near the disc and have other thermally detrimental side effects. Some recent studies have shown that the amount of thermal energy provided to the posterior annulus by the IDET procedure is insufficient to cause either shrinkage/strengthening of the posterior annulus or ablation of the pain-sensing posterior annular nerve endings.

Several prior art references disclose methods for applying energy to the interior of an intervertebral disc by invading the disc with a needle or catheter. For example, U.S. Pat. No. 5,865,833 to Daikuzono is directed to a device for laser treatment. The Daikuzono device is for a discectomy procedure and for removal of intervertebral disc tissue, not to avoid a discectomy or to preserve disc tissue or ablate posterior annulus pain-sensing nerve endings. The Daikuzono method uses a hollow needle that is advanced into the center of an intervertebral disc, and then disc tissue is vaporized with laser energy and the vapor removed through the hollow needle. The hollow needle invasively punctures the disc.

U.S. Pat. Nos. 6,007,570, 6,073,051, 6,095,149, and 6,122,549 to Sharkey et al. (the "Sharkey references") are directed to methods for treating an intervertebral disc and to devices with tip portions for performing various functions on a disc. Externally guidable catheters having one lumen or several lumina puncture the annulus fibrosis of an intervertebral disc and are inserted into the nucleus pulposus at the center of the disc. Functional tips on the distal ends of the catheters add or remove material or deliver energy. The Sharkey references also disclose injecting a sealant into fissures in the annulus fibrosis. The methods and devices of the Sharkey references have the advantage of treating an intervertebral disc from the inside, thereby using the annulus fibrosis of a disc as thermal insulation from the spinal canal. The Sharkey methods and devices, however, have the disadvantage of not being able to reach many types of bulges, ruptures, or areas of injury in or near the outer layers of the annulus fibrosis. Further, because they puncture the disc, the Sharkey catheters are invasive and larger puncture holes are needed in order to use larger functional tips. The Sharkey methods and devices do not provide a noninvasive external approach to disc repair, and require maneuvering a catheter inside an intervertebral disc. They also do not ablate nerve endings in the posterior annulus and do not shrink/strengthen the posterior annulus.

Known prior art methods for treating an injured intervertebral disc are invasive to the disc, do not shrink/strengthen the posterior annulus, do not ablate the pain-sensing nerve endings in the posterior annulus, and may be thermally unsafe to vulnerable tissues around the spine.

BRIEF SUMMARY OF THE INVENTION

The present invention provides a method and apparatus for shrinking and strengthening the cartilaginous or collagenous material ("collagen") near an injury in the annulus fibrosis or the nucleus pulposus of one or more intervertebral discs. The present invention may allow a spine surgeon to avoid a discectomy and removal of the nucleus pulposus during a laminectomy operation.

The present invention's epidural and extradiscal approach to repairing a disc prevents the invasion of a disc with a needle or catheter. Needle and catheter methods puncture the intervertebral disc being treated, thereby exacerbating the very condition sought to be cured or may introduce infection into the nerve space.

The present invention may eliminate or greatly reduce discogenic pain by thermally destroying nerve endings that transmit pain sensation from the posterior annulus. The surface area of the posterior annulus that can be treated for the reduction of discogenic pain is not limited as in prior art methods that deliver energy from a device inside the disc.

During thermal treatment by the present invention, vulnerable tissues near a disc undergoing treatment may be thermally insulated or cooled and/or displaced away from the thermal energy and thereby protected from potentially destructive heat. Laser embodiments of the present invention may achieve thermocoagulation of disc tissue by short laser bursts that confine heating to the disc. This thermal confinement combined with posterior displacement of neural structures may protect these vulnerable tissues near a disc without requiring insulation or cooling of the vulnerable tissues.

The present invention's strengthening of collagen may result in the reduction of future incidents of disc herniation, reduction of spinal nerve-root impingement, and reduction of discogenic pain arising from nerve endings in posterior annulus.

The present invention is directed to an apparatus for thermally treating intervertebral discs using an energy application head having an energy application region and a tissue protecting region. A control member is operationally connected to the energy application head to control the energy application head during treatment of an intervertebral disc.

The present invention also includes a method for thermally treating an injured intervertebral disc while thermally protecting vulnerable tissues. The method includes gaining access to a vertebral column, epidurally approaching the posterior aspect of an injured intervertebral disc, and evaluating the extent of disc injury. The evaluation preferably includes calculating an amount of energy needed to thermally refurbish the intervertebral disc. Energy is applied to the posterior aspect of the injured intervertebral disc while maintaining a safe temperature in vulnerable tissues near the disc. The energy delivered is monitored and the shrinkage and strengthening of the disc may be observed to determine if additional energy is required by the disc or adjacent discs. Further energy may be applied to other posterior areas of the disc to reduce pain. The steps of this method may be performed in alternate order. Steps that are unnecessary in a specific surgery may be omitted.

The foregoing and other objectives, features, and advantages of the invention will be more readily understood upon consideration of the following detailed description of the invention, taken in conjunction with the accompanying drawings.

BRIEF DESCRIPTION OF THE SEVERAL VIEWS OF THE DRAWING

FIG. 5 is a top view of an exemplary head and part of an exemplary control member of one preferred embodiment of the disc refurbisher of the present invention.

FIG. 6 is a side view of the exemplary head and a cut-away view of part of the exemplary control member of FIG. 5.

FIG. 7 is a side view of an exemplary head of one preferred embodiment of the disc refurbisher of the present invention showing an expanded head shape.

FIG. 8 is a side view of an exemplary head of one preferred embodiment of the disc refurbisher of the present invention showing a contracted head shape.

FIG. 9 is a side view of an exemplary head of one preferred embodiment of the disc refurbisher of the present invention showing a flat energy application region.

FIG. 10 is a side view of an exemplary head of one preferred embodiment of the disc refurbisher of the present invention showing a concave energy application region.

FIG. 11 is a side view of an exemplary head of one preferred embodiment of the disc refurbisher of the present invention showing a convex energy application region.

FIG. 12 is a side view of an exemplary head of one preferred embodiment of the disc refurbisher of the present invention showing a malleable energy application region.

FIG. 13 is a side and partial cut-away view of a section of an exemplary control member of one preferred embodiment of the present invention showing optional operational members.

FIG. 14 is a cross-sectional side view of an exemplary head of one preferred embodiment of the disc refurbisher of the present invention showing control members operationally connected to a head.

FIG. 15 is a cross-sectional side view of an exemplary head of one preferred embodiment of the disc refurbisher of the present invention showing an integrated defocused laser as a energy applicator.

FIG. 16 is a cross-sectional side view of an exemplary head of one preferred embodiment of the disc refurbisher of the present invention showing an external defocused laser as an energy applicator.

FIG. 17 is a cross-sectional side view of an exemplary head of one preferred embodiment of the disc refurbisher of the present invention showing a lens as an energy applicator.

FIG. 18 is a cross-sectional side view of an exemplary head of one preferred embodiment of the disc refurbisher of the present invention showing electrodes as energy applicators.

FIG. 19 is a cross-sectional side view of an exemplary head of one preferred embodiment of the disc refurbisher of the present invention showing a wire as an energy applicator.

FIG. 20 is a cross-sectional side view of an exemplary head of one preferred embodiment of the disc refurbisher of the present invention showing a light bulb as an energy applicator.

FIG. 21 is a cross-sectional side view of an exemplary head of one preferred embodiment of the disc refurbisher of the present invention showing a resistive heating element as an energy applicator.

FIG. 22 is a cross-sectional side view of an exemplary head of one preferred embodiment of the disc refurbisher of the present invention showing an ultrasonic transducer as an energy applicator.

DETAILED DESCRIPTION OF THE INVENTION

Epidural thermal posterior annuloplasty is a method for shrinking and strengthening the collagen at an injury in the annulus fibrosis of the nucleus pulposus of one or more intervertebral discs. This method of the present invention differs from previous methods by treating one or more intervertebral discs from an epidural, extradiscal approach while protecting vulnerable tissue near the disc. Central to the method of the present invention is a disc refurbisher device having an energy source—for example, a defocused laser—that heats the injured tissue without vaporizing it. The heating may cause shrinkage of the collagen resulting in a stronger, tighter intervertebral disc and desirable destruction of microscopic pain-causing nerve endings in the intervertebral disc being treated. The intervertebral disc is not physically invaded, and tissues surrounding the disc remain safe.

Description of a Preferred Method of the Present Invention

A preferred embodiment of a method of the present invention is an epidural, extradiscal, thermal treatment for repairing an injured intervertebral disc that protects vulnerable tissues near the disc and does not physically invade the disc. Several adjacent discs may be treated by manipulating a disc refurbisher in the epidural space.

Figure 1:
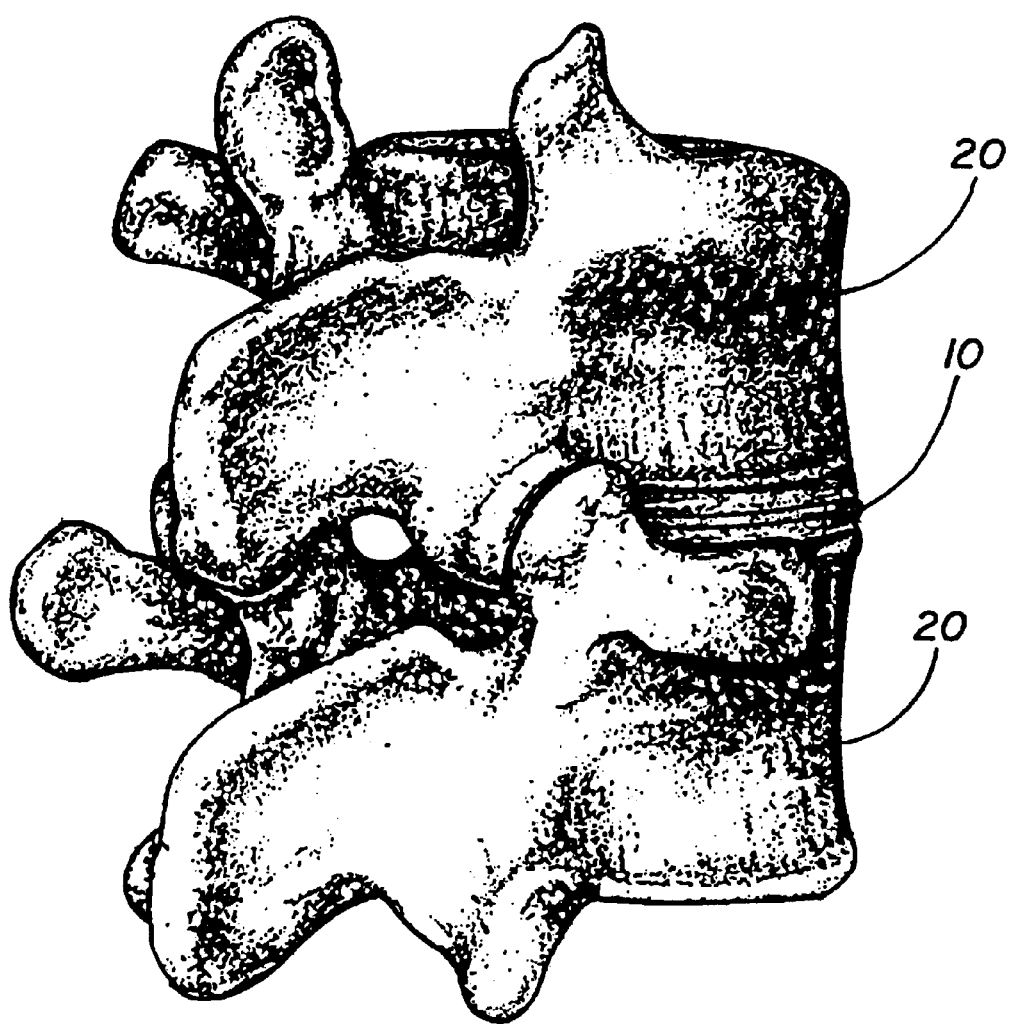
FIG. 1 is a posterolateral view of two adjacent lumbar vertebrae.
Figure 2:
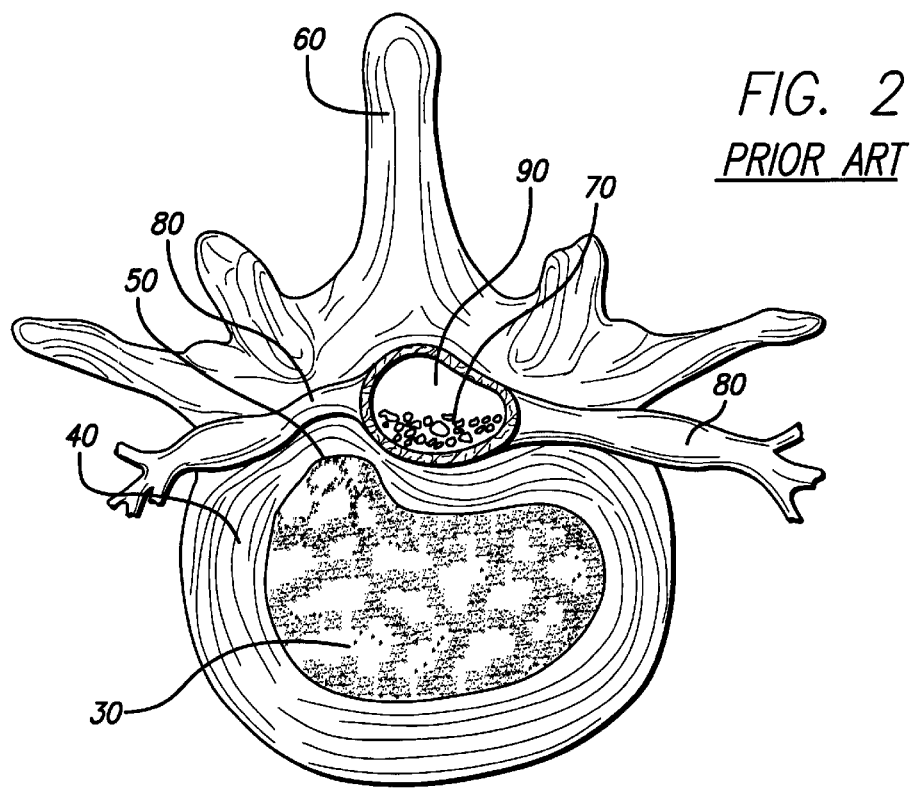
FIG. 2 is a transverse cross-section through the spine showing a ruptured intervertebral disc, the spinal canal and cauda equina, and the bony processes of a vertebra.
Figure 4:
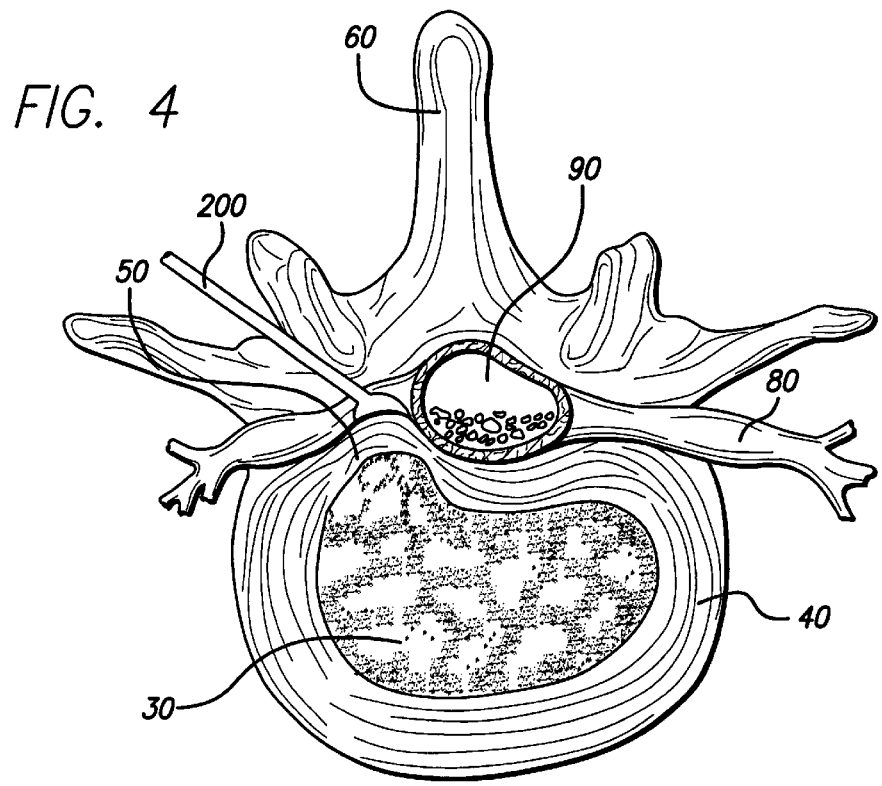
FIG. 4 is a transverse cross-section through a spine with an exemplary disc refurbisher head positioned near the posterior annulus.
Figure 3:
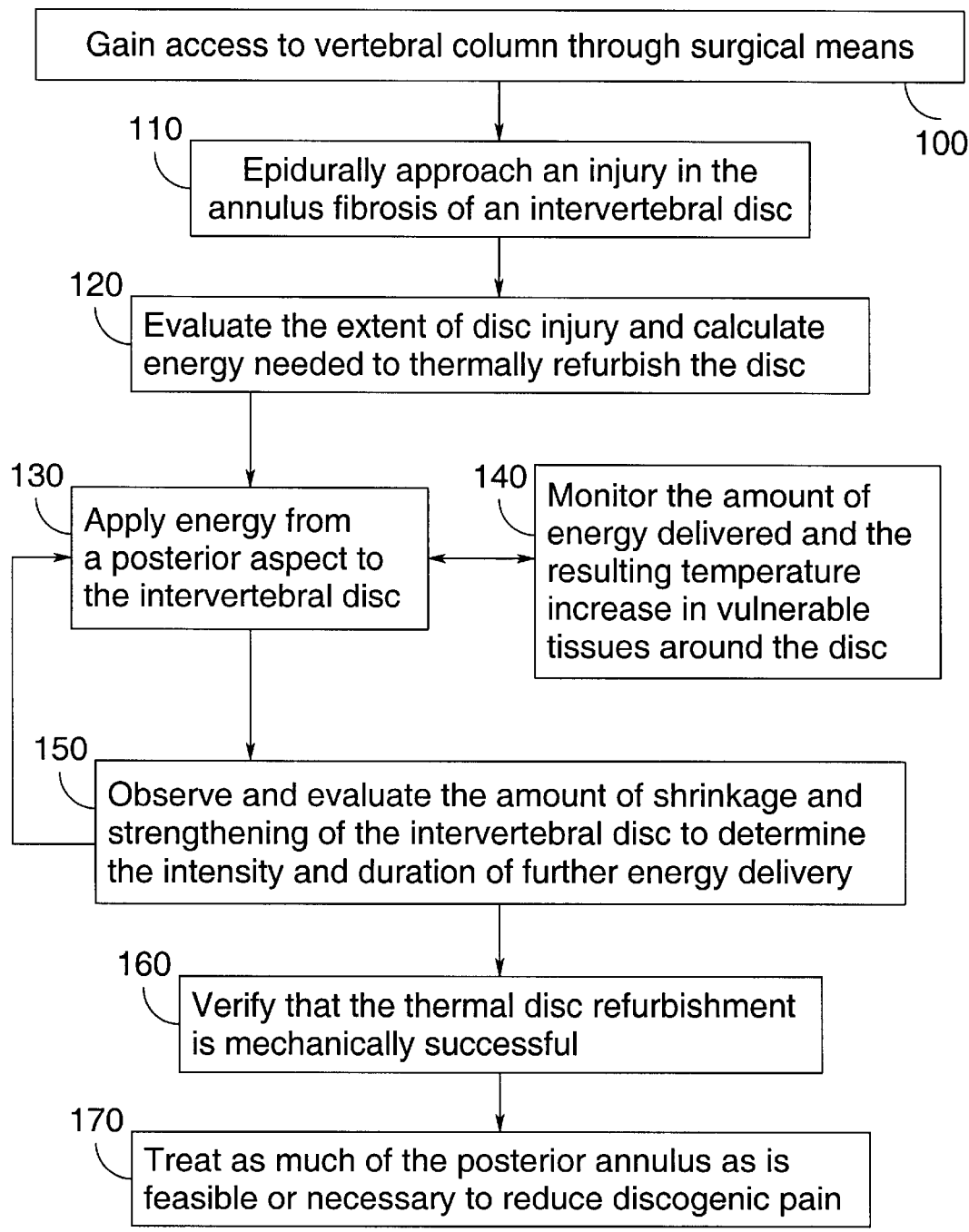
FIG. 3 is a flowchart of a preferred method of the present invention for thermal treatment of a bulging, ruptured, or injured intervertebral disc.

FIG. 3 shows an exemplary method of treatment. As shown, access is gained to the vertebral column through surgical means 100. An injury in or near the annulus fibrosis of an intervertebral disc is approached epidurally 110. The extent of disc injury is evaluated and the amount of energy needed to thermally refurbish the disc is calculated 120. Energy is then applied to the injured intervertebral disc from a posterior position 130. The application of energy 130 may be carried out by an instrument. FIG. 4 shows one preferred embodiment of an instrument for treating an intervertebral disc ("disc refurbisher") 200 that may be used in the preferred method. The disc refurbisher is inserted epidurally from a posterior approach, remaining outside the rings of the annulus fibrosis 40 of the intervertebral disc, and is used to apply energy to an exemplary injury 50 in the annulus fibrosis 40. The amount of energy delivered in the preferred method may be monitored simultaneously with the temperature of vulnerable tissues around the disc 140. Sensors and instruments including but not limited to thermometers, thermistors, thyristors, phosphor-coated optic fibers, and temperature-sensitive crystals may monitor temperatures and pressures of delivered energy at the energy application site. Instruments such as micro-forceps, biopsy samplers, and aspirators may be inserted through a lumen in the disc refurbisher. Matter and bodily tissues, such as vascular lesion tissue, sequestrated disc fragments, and synovial cyst tissue may be removed through a lumen in the disc refurbisher. The amount of shrinkage and strengthening of the collagen in and around the injury is observed and evaluated to determine the intensity and duration of further energy delivery 150. The observation and evaluation of shrinkage and strengthening may be made using unaided vision. Alternately, at least one lens, mirror, camera, fiber-optic device, or other optical device may be used. Observation and evaluation could also be made with a mechanical probe. The mechanical success of the thermal disc refurbishment is preferably verified 160. Further energy for deadening sensory nerve endings in the annulus may be delivered to as much of the posterior annulus as is feasible or necessary to reduce discogenic pain 170. The surgical access site or sites are closed. The steps may be performed in alternate order.

Description of a Preferred Apparatus of the Present Invention

A preferred apparatus embodiment of the present invention is a disc refurbisher that may be used intraoperatively, but not necessarily for percutaneous spine surgery. A disc refurbisher has a shape for approaching an intervertebral disc epidurally. In one preferred embodiment, the disc refurbisher has an energy delivery system for treating at least one intervertebral disc. In an alternate preferred embodiment the disc refurbisher has additional thermal protection features for safeguarding tissues that surround an intervertebral disc.

Shape and Physical Geometry of Preferred Apparatus Embodiments

The exemplary disc refurbisher shown in FIGS. 5 and 6 has an energy applicator such as a head 180 operationally connected to a control member 190 such as a longitudinal shaft member.

A preferred energy application head ("head") of the disc refurbisher is preferably shaped so that the approach to an injured intervertebral disc may be epidural. To approach epidurally, the surface of the exemplary head 180 of the instrument is preferably smoothly contoured to glide over the posterior annulus and reach the injury site without snagging or tearing the nearby nerve roots, epidural blood vessels, dura, and thecal sac. The smooth, rounded edges 210 of the anterior portion of the head lift and displace the dura to epidurally gain access to the site of injury at the annulus fibrosis and reduce the thermal effect on the dura and neural structures. The head is preferably thinner at its smooth rounded edges 210 than at its exemplary domed center 220, allowing easy insertion between tissue layers and separation of tissues as the instrument is advanced to the injury site or moved from side to side. The shape facilitates treating adjacent discs by manipulating the disc refurbisher in the epidural space.

A wedge-shaped cross-sectional or longitudinal geometry of an exemplary head, such as the head shown in FIGS. 5 and 6, separates and thereby insulates the nerve roots, dura, and thecal sacs of the spinal canal on one side of the instrument from the energy delivery occurring at the surface of the intervertebral disc on another side of the instrument. The smooth, rounded edges 210 of the anterior portion of the exemplary head are relatively thin and slope to a relatively thick region under the exemplary domed center 220 creating a wedge-shaped head geometry.

The wedge-shaped exemplary head has a maximum wedge thickness that may automatically lift vulnerable tissues a calculated safe distance away from a site of energy application as the instrument is moved. A calculated safe distance may be proportional to the amount and duration of energy being applied or proportional to temperatures induced in the disc. In one variation shown in FIGS. 7 and 8, the maximum wedge thickness of a head is variable and automatically expands 300 or contracts 310 in proportion to the amount of energy being delivered. The variation in thickness may be accomplished mechanically or by using an inflatable top portion that expands under air or liquid pressure.

In FIGS. 9–12, the energy application regions of preferred head embodiments may be flat 320, concave 330, convex 340, or malleable 350. Initially, an embodiment with a concave energy application region may be used to approximate the contour of a bulging area of disc, followed by an embodiment with a flat energy application region to impart a finished surface to the shrunken and tightened collagen. Each embodiment is operationally connected to at least one controlling member 190.

A head embodiment may have a diameter of approximately five millimeters, but a wider head could be used for tissue shielding or a wider application of energy. Alternately, a set of disc refurbishers may have heads of various useful shapes and sizes. Still another alternative disc refurbisher may have a head that varies in size using mechanical means.

In FIGS. 5 and 6, an operational steering and controlling member ("control member" 190) such as an exemplary longitudinal shaft member may be attached to a disc refurbisher head 180 at an angle from the plane of the head of between 0° and 180°, shown as 25°. Alternately, the control member 190 may be rotatably connected to the head. The control member 190 may be stiff, flexible, malleable, or articulated to provide physical control of disc refurbisher movement. In FIG. 13, a portion of a control member 190 is shown as optionally containing operational members, such as at least one wire 360, fiber-optic strand 370, hollow tube 380, or radio control device 390. The hollow tube 380 or lumen may allow instruments such as micro-forceps, biopsy samplers, and aspirators to be inserted through the disc refurbisher to the site of treatment. Matter and bodily tissues, such as blood, irrigation fluid, vascular lesion tissue, sequestrated disc fragments, and synovial cyst tissue may be removed through the hollow tube 380 in the disc refurbisher. Several lumina may be used to provide irrigation to the site of treatment. The control member 190 may also contain a moving mechanical link, such as a rotating inner shaft 400 or an oscillating inner member. Alternately, as shown in FIG. 14, control members 410 may be one or more wires, radio control mechanisms, beams of light, or any other control mechanism. One or more control members 410 may be attached in various useful configurations and at various useful angles.

Energy Application Using Preferred Apparatus Embodiments of the Present Invention As shown in FIG. 6, a disc refurbisher embodiment of the present invention may deliver energy to an intervertebral disc from an energy applicator on an energy application region, shown as the bottom side 500, of the instrument's head 180. Other surfaces than the shown bottom side could be used as the energy application region in other embodiments. Energy applicators may be positioned on, consist of, or deliver energy through an energy application region depending on the type of energy applicator being used. As shown in FIGS. 15–22, energy applicators may include one or more lasers 420, fiber-optic strands 430, lenses 440, electrodes 450, wires 460, light bulbs 470, heating elements 480, and ultrasound transducers 490. A disc refurbisher may have more than one energy-delivering side and each energy-delivering side may have more than one energy application region.

The energy applicator may be supplied with energy from a source external to the head, for example laser energy transmitted by optical fibers from an external laser to the head. Alternately, the energy applicator may generate or convert energy within the head, for example electric current from an external source carried to a resistive heating element within the head. If energy is supplied to the head, transmission of energy through a control member may be through any energy transmission means, such as wire, lumen, thermal conductor, or fiber-optic strand. In FIG. 6, an exemplary fiber-optic bundle 510 fans out 520 into a useful pattern at the energy application region, shown as the flat bottom 500 of the head.

The disc refurbisher may deliver electromagnetic energy, including but not limited to radio waves, microwaves, infrared light, visible light, and ultraviolet light. The electromagnetic energy may be in incoherent or laser form. The energy in laser form may be collimated or defocused. The energy delivered to a disc may also be electric current, ultrasound waves, or thermal energy from a heating element.

Laser Application of Energy

One exemplary preferred embodiment uses laser energy. The interaction of laser energy with the collagen of an intervertebral disc has photothermal, photomechanical, and photochemical components. The present invention takes advantage of all three effects.

Figures 23, 24:
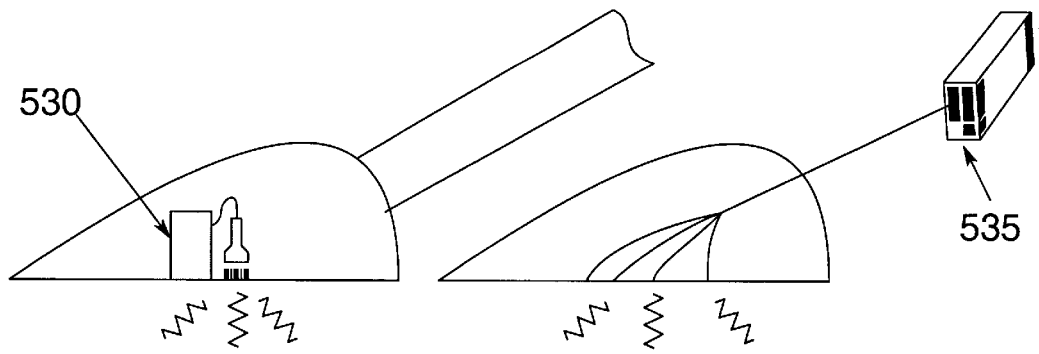
FIG. 23 is a cross-sectional side view of an exemplary head of one preferred embodiment of the disc refurbisher of the present invention showing an integrated defocused laser for slowly applying thermal energy.
FIG. 24 is a cross-sectional side view of an exemplary head of one preferred embodiment of the disc refurbisher of the present invention showing an external defocused laser for slowly applying thermal energy.

Photothermally, photons absorbed by a disc heat the disc and thermally coagulate the collagen ("thermocoagulation"). Thermocoagulation may be achieved by applying energy with a continuous or long-pulse laser using microsecond or millesecond pulses. FIGS. 23 and 24 show preferred embodiments of a disc refurbisher in which defocused lasers are used to provide a relatively slow, areawide application of heat. FIG. 23 shows an integrated defocused laser 530. FIG. 24 shows an external defocused laser 535 that may use a fiber-optic bundle in the transmission of defocused energy. Since lasers are monochromatic, wavelengths may be selected that would efficiently match the peak absorption range of collagen. To optimize the relatively slow application of heat using a defocused laser embodiment, a photosensitive chemical reagent that would enhance or modify the absorption of selected laser energy could be painted or sprayed onto the target and exposed to the laser output.

Figures 25, 26:
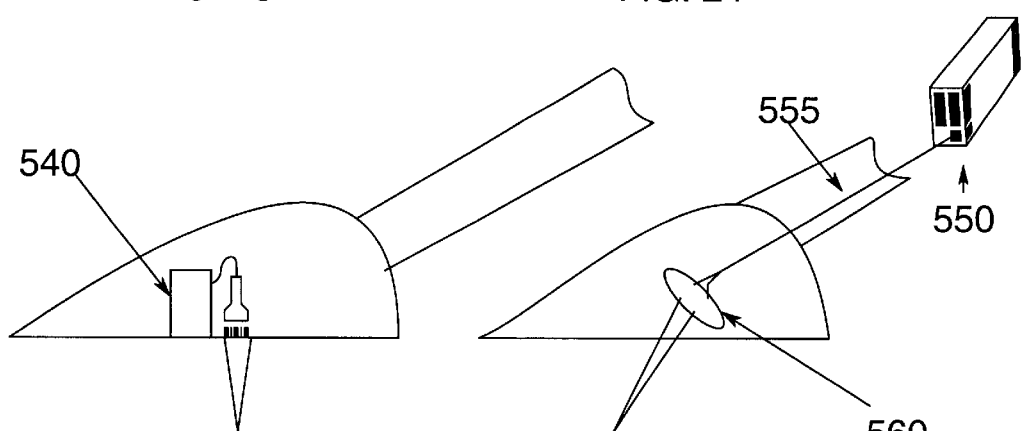
FIG. 25 is a cross-sectional side view of an exemplary head of one preferred embodiment of the disc refurbisher of the present invention showing an integrated collimated laser for applying thermally confined energy.
FIG. 26 is a cross-sectional side view of an exemplary head of one preferred embodiment of the disc refurbisher of the present invention showing an external collimated laser for applying thermally confined energy.

Alternately, laser energy for thermocoagulation may be collimated. FIGS. 25 and 26 show preferred embodiments in which the energy applicator of a preferred disc refurbisher is a collimated laser. In FIG. 25, an integrated laser 540 generates the collimated laser energy. In FIG. 26, an external laser 550 generates collimated laser energy that is focused into optical fibers 555 for delivery to the treatment site and optionally focused to very small areas by at least one lens 560. The laser light may be short-pulsed, which would make the delivery of relatively large amounts of energy, such as gigawatts, possible in very short time periods, such as nanoseconds. Short-pulsed laser bursts may achieve thermal confinement, the desirable rapid buildup of heat in a treatment site before thermal diffusion can dissipate the heat, preventing the heating of vulnerable tissues near the disc.

Photomechanically, the laser may be used for vaporizing undesirable tissues or spallation of the surface layer of the disc, in addition to overall thermocoagulation of the collagen. Spallation achieves surface modification by removing only superficial collagen layers. During disc surgery, at the free boundary of an air/collagen interface, collagen expands at the surface when exposed to a rapid laser pulse, then snaps back with elastic force. The expansion creates positive pressure, but the recoil creates negative pressure. If the negative pressure exceeds the strength of the collagen, then the surface layer breaks. A thin layer of collagen is ejected. Such breaks or spall planes induced in the surface of the collagen could be used to shape a finished surface of the disc or to eject unwanted bulge material at the beginning of a disc refurbishment procedure. A vaporizing laser may be used to remove undesirable tissues, such as excess collagen, vascular lesion tissue, sequestrated disc fragments, and synovial cysts.

Photochemically, the therapeutic application of energy to an intervertebral disc may cause several physiological changes. Once the delivered laser or other energy is translated into thermal energy in the collagen in or near an injury in the annulus fibrosis, a desirable microscopic breakdown of pain-causing nerve ending tissue may occur if so desired by the practitioner. The therapeutic destruction of nerve endings begins to occur when the temperature of the annulus reaches approximately 45° C. At temperatures above 60° C., changes in the cross-linked structure of the collagen near an injury in the annulus begin to occur. The thermal denaturing of the collagen protein molecules causes thermocoagulation and desirable shrinkage of the bulging, ruptured, or injured annulus fibrosis. The thermocoagulation is accompanied by a simultaneous strengthening of the annulus fibrosis.

Photochemical welding of injuries, for example tears, in the annulus fibrosis may also be accomplished by using a chemical reagent containing an adhesive photoactivated by laser light.

Thermal Protection of Vulnerable Tissues by Preferred Apparatus Embodiments

The manner of energy delivery may forestall the need to protect vulnerable tissues, as when a pulsed laser achieves thermocoagulation with thermal confinement to the disc. In FIG. 6, when thermal protection is needed because of the type of energy applicator being used, thermally vulnerable tissues near a site of energy application to a disc may be protected by an exemplary tissue protecting region 600 of an energy application head 180. A tissue protecting region 600 may contain a thermal protector, including but not limited to at least one optional insulation layer 610, and/or an optional cooling system 620. One or more optional layers of insulation 610 or a cooling system 620 in a preferred embodiment of a disc refurbisher may thermally separate an energy applying side of a disc refurbisher head from a tissue protecting side. The tissue protecting region may also result from a disc refurbisher shape that lifts vulnerable tissues away from a site of energy application.

A disc refurbisher may be cooled by internal or external airflow, or by fluid or liquid pumped from a cooling reservoir such as a controlled temperature bath. As shown in FIG. 6, the cooling system of one preferred embodiment of a disc refurbisher may incorporate internal cooling tubes 620. Refrigerants may be used in the cooling tubes to provide mild or aggressive cooling. Cooling may be controlled by mechanism or computer to counteract a proportional amount of heat being generated by a disc refurbisher. Alternately, the cooling may be accomplished by at least one thermocouple in contact with the tissue protecting region of a head embodiment. The thermocouple may constitute all or part of the material surface of a tissue protecting region. As another alternative, heat-pipe technology currently used to cool state-of-the-art microprocessor chips may also be used as a preferred thermal protector. The tissue protecting side may incorporate metals such as aluminum alloys or other materials having high heat conductivity and heat-sinking properties to transfer heat to a cooling system.

A preferred embodiment of a disc refurbisher, shown in FIG. 6, has an energy delivery system, shown as a fiber-optic bundle 510 and 520, surrounded by a cooling system shown as a layer of insulation 610, cooling tubes 620, and a thermally conductive metal outer surface.

Sensors and other instruments including but not limited to thermometers, thermistors, thyristors, phosphor-coated optic fibers, and temperature-sensitive crystals may monitor temperatures at the energy application and tissue protecting regions of a disc refurbisher and adjust the energy applicators and cooling systems to maintain selected temperatures. The control of heating and cooling may be by thermostat, electronic circuit, computer, or any other mechanism able to dynamically adjust temperature.

Other Embodiments and Features of a Disc Refurbisher

All embodiments of a disc refurbisher may be robotically manipulable. At least one robotic mechanism may be used to place a disc refurbisher at the surface of a disc, to apply energy, and to move a disc refurbisher around the posterior annulus of a disc. A disc refurbisher under robotic control may apply computer-controlled amounts of energy in computer-controlled patterns and amounts.

A disc refurbisher may optionally contain at least one tube or lumen for transmitting material to and from a treatment site. A lumen may transmit a gas or fluid such as compressed air or water to the treatment site for uses including but not limited to irrigation, clearing away debris, and cooling. The lumen may also be a suction channel for vacuuming debris from the treatment site. The lumen may allow instruments such as micro-forceps, biopsy samplers, aspirators, and other surgical tools to be inserted through the disc refurbisher to the site of treatment. Matter and bodily tissues, such as blood, irrigation fluid, vascular lesion tissue, sequestrated disc fragments, synovial cyst tissue, and vaporized tissue may be removed through one or more lumina.

Figures 27, 28:
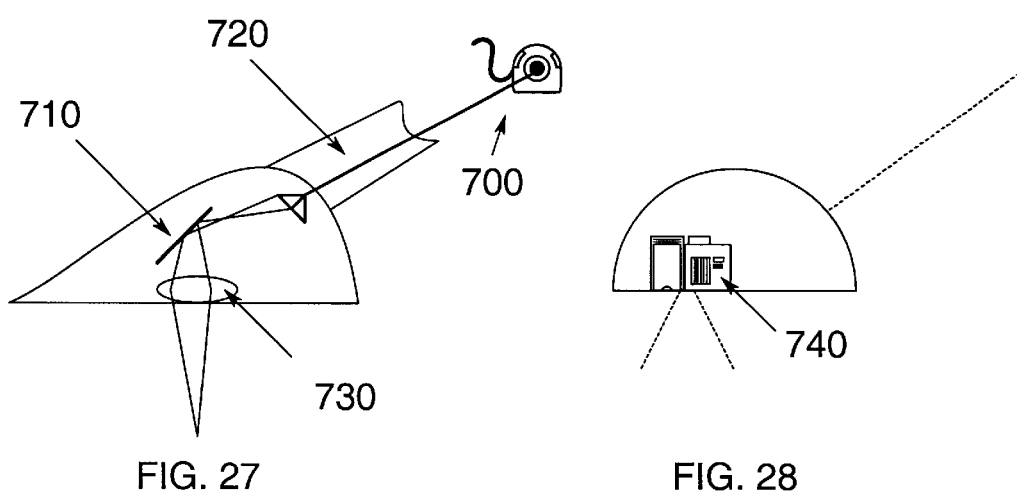
FIG. 27 is a cross-sectional side view of an exemplary head of one preferred embodiment of the disc refurbisher of the present invention showing optional optical devices for visualizing a treatment area.
FIG. 28 is a cross-sectional side view of an exemplary head of one preferred embodiment of the disc refurbisher of the present invention showing an exemplary instrument for performing a physical measurement.

In FIG. 27, preferred embodiments of a disc refurbisher may optionally incorporate at least one tissue visualizing instrument. Optics for visualizing the treatment site—for example, at least one camera 700, mirror 710, fiber-optic bundle 720, or lens 730—may be incorporated into the energy application head. The optics may transmit human-readable visual images from the treatment site or may transmit machine-readable feedback about energy being delivered and its effect on tissue. The disc refurbisher may transmit human-readable images that are displayable on a monitor or other medical imaging equipment.

At least one physical measuring instrument may be added to preferred disc refurbisher embodiments. FIG. 28 shows an exemplary instrument 740 integrated into an energy application head that may measure pressures, distances, areas, or volumes with a human body. Other physical measurements may be performed by a disc refurbisher using instruments integrated or external to a disc refurbisher head.

The terms and expressions that have been employed in the foregoing specification are used as terms of description and not of limitation and are not intended to exclude equivalents of the features shown and described or portions of them. The scope of the invention is defined and limited only by the claims that follow.

What is claimed is:

1. An apparatus for thermally treating at least one intervertebral disc, comprising:
   (a) an energy application head having an energy application region and a tissue protecting region;
   (b) a control member operationally connected to said energy application head, said control member suitable for controlling said energy application head during treatment of said at least one intervertebral disc; and
   (c) said energy application head having a distance between said energy application region and said tissue protecting region wherein said distance is variable to protect tissue of said at least one intervertebral disc.

2. An apparatus for thermally treating at least one intervertebral disc, comprising:
   (a) an energy application head having an energy application region and a tissue protecting region;
   (b) a control member operationally connected to said energy application head, said control member suitable for controlling said energy application head during treatment of said at least one intervertebral disc; and
   (c) said energy application head having a distance between said energy application region and said tissue protecting region wherein said distance automatically varies to protect tissue of said at least one intervertebral disc.

3. An apparatus for thermally treating at least one intervertebral disc, comprising:
   (a) an energy application head having an energy application region and a tissue protecting region;
   (b) a control member operationally connected to said energy application head, said control member suitable for controlling said energy application head during treatment of said at least one intervertebral disc; and
   (c) said energy application head having a distance between said energy application region and said tissue protecting region wherein said distance is variable in proportion to an amount of energy being delivered to said at least one intervertebral disc.

4. An apparatus for thermally treating at least one intervertebral disc, comprising:
   (a) an energy application head having an energy application region and a tissue protecting region;
   (b) a control member operationally connected to said energy application head, said control member suitable for controlling said energy application head during treatment of said at least one intervertebral disc; and
   (c) said energy application head having a distance between said energy application region and said tissue protecting region wherein said distance automatically varies in proportion to an amount of energy being delivered to said at least one intervertebral disc.

5. An apparatus for thermally treating at least one intervertebral disc, comprising:
   (a) an energy application head having an energy application region and a tissue protecting region, said energy application head being wedge-shaped;
   (b) a control member operationally connected to said energy application head, said control member suitable for controlling said energy application head during treatment of said at least one intervertebral disc; and
   (c) said energy application head having a distance between said energy application region and said tissue protecting region wherein said distance automatically varies in proportion to an amount of energy being delivered to said at least one intervertebral disc.

6. The apparatus of claim 5, wherein said energy application head has a smooth surface suitable for gliding over surfaces of an annulus fibrosis without snagging other tissues.

7. The apparatus of claim 5, said energy application head further comprising at least one instrument selected from the group consisting of:
   (a) a temperature measuring instrument;
   (b) a tissue visualizing instrument
   (c) an energy measuring instrument;
   (d) a distance measuring instrument;
   (e) an area measuring instrument;
   (f) a pressure measuring instrument; and
   (g) a volume measuring instrument.

8. The apparatus of claim 5, said energy application head further comprising at least one energy applicator selected from the group consisting of:
   (a) a laser;
   (b) a fiber-optic strand;
   (c) a lens;

(d) an electrode;
(e) a wire;
(f) a light bulb;
(g) a heating element; and
(h) an ultrasound transducer.

9. The apparatus of claim 5, said control member further comprising at least one member selected from the group consisting of:
   (a) a wire;
   (b) a fiber-optic strand;
   (c) one or more hollow tubes;
   (d) a radio control mechanism;
   (e) a moving mechanical link; and
   (f) a beam of light;
   (g) a lumen for adding and removing instruments;
   (h) a lumen for adding and removing tissue; and
   (i) a lumen for irrigating.

10. The apparatus of claim 5, wherein said energy application head applies energy selected from the group consisting of:
   (a) electric current;
   (b) radio frequency waves;
   (c) microwaves;
   (d) infrared waves;
   (e) visible light waves;
   (f) ultraviolet waves;
   (g) ultrasonic sound waves; and
   (h) conductive thermal energy.

11. The apparatus of claim 10, said energy further comprising energy in a form selected from the group consisting of:
   (a) incoherent electromagnetic radiation;
   (b) defocused laser energy; and
   (c) collimated laser energy.

12. The apparatus of claim 5, said tissue protecting region further comprising at least one thermal protector for protecting vulnerable tissues from energy applied by said energy application head.

13. The apparatus of claim 12, wherein said at least one thermal protector is selected from the group consisting of:
   (a) at least one layer of insulation;
   (b) airflow coolant;
   (c) liquid coolant;
   (d) coolant from a refrigeration system;
   (e) a thermocouple; and
   (f) a heat-pipe.

14. An apparatus for thermally treating at least one intervertebral disc, comprising:
   (a) an energy application head having an energy application region and a tissue protecting region;
   (b) a control member operationally connected to said energy application head, said control member suitable for controlling said energy application head during treatment of said at least one intervertebral disc;
   (c) said energy application head having a thin insertion edge sloped to a thick region for lifting vulnerable tissues away from a site of energy application to said at least one intervertebral disc; and
   (d) said energy application head having a distance between said energy application region and said tissue protecting region wherein said distance automatically varies in proportion to an amount of energy being delivered to said at least one intervertebral disc.

15. The apparatus of claim 14, wherein said energy application head has a smooth surface suitable for gliding over surfaces of an annulus fibrosis without snagging other tissues.

16. The apparatus of claim 14, said energy application head further comprising at least one instrument selected from the group consisting of:
   (a) a temperature measuring instrument;
   (b) a tissue visualizing instrument
   (c) an energy measuring instrument;
   (d) a distance measuring instrument;
   (e) an area measuring instrument;
   (f) a pressure measuring instrument; and
   (g) a volume measuring instrument.

17. The apparatus of claim 14, said energy application head further comprising at least one energy applicator selected from the group consisting of:
   (a) a laser;
   (b) a fiber-optic strand;
   (c) a lens;
   (d) an electrode;
   (e) a wire;
   (f) a light bulb;
   (g) a heating element; and
   (h) an ultrasound transducer.

18. The apparatus of claim 14, said control member further comprising at least one member selected from the group consisting of:
   (a) a wire;
   (b) a fiber-optic strand;
   (c) one or more hollow tubes;
   (d) a radio control mechanism;
   (e) a moving mechanical link;
   (f) a beam of light;
   (g) a lumen for adding and removing instruments;
   (h) a lumen for adding and removing tissue; and
   (i) a lumen for irrigating.

19. The apparatus of claim 14, wherein said energy application head applies energy selected from the group consisting of:
   (a) electric current;
   (b) radio frequency waves;
   (c) microwaves;
   (d) infrared waves;
   (e) visible light waves;
   (f) ultraviolet waves;
   (g) ultrasonic sound waves; and
   (h) conductive thermal energy.

20. The apparatus of claim 19, said energy further comprising energy in a form selected from the group consisting of:
   (a) incoherent electromagnetic radiation;
   (b) defocused laser energy; and
   (c) collimated laser energy.

21. The apparatus of claim 14, said tissue protecting region further comprising at least one thermal protector for protecting vulnerable tissues from energy applied by said energy application head.

22. The apparatus of claim 21, wherein said at least one thermal protector is selected from the group consisting of:
(a) at least one layer of insulation;
(b) airflow coolant;
(c) liquid coolant;
(d) coolant from a refrigeration system;
(e) a thermocouple; and
(f) a heat-pipe.

23. A method for epidurally treating at least one intervertebral disc using a disc refurbisher, said method comprising the steps of:
(a) gaining access to a vertebral column;
(b) epidurally approaching the posterior aspect of said at least one intervertebral disc;
(c) applying energy to a posterior aspect of said at least one intervertebral disc using said disc refurbisher, said disc refurbisher having an energy application head having an energy application head having an energy application region and a tissue protecting region, said energy application head having a distance between said energy application region and said tissue protecting region; and
(d) varying said distance between said energy application region and said tissue protecting region to protect vulnerable tissues associated with said at least one intervertebral disc from said energy.

24. The method of claim 23, further comprising at least one step selected from the group of steps consisting of:
(a) evaluating an extent of disc injury;
(b) calculating an amount of energy needed to thermally refurbish said at least one intervertebral disc;
(c) monitoring an amount of energy delivered and a temperature in vulnerable tissues around said at least one intervertebral disc;
(d) observing and evaluating an amount of shrinkage and strengthening of said at least one intervertebral disc to determine an intensity and duration of further energy delivery; and
(e) verifying that said shrinkage and strengthening of said at least one intervertebral disc is mechanically successful.

25. The method of claim 23, further comprising the step of maintaining a safe temperature in vulnerable tissues near said at least one intervertebral disc.

26. A method for thermally treating an intervertebral disc while thermally protecting vulnerable tissues, said method comprising the steps of:
(a) providing a disc refurbisher, said disc refurbisher comprising:
(i) an energy application head having an energy application region and a tissue protecting region, said energy application head having a distance between said energy application region and said tissue protecting region; and
(ii) a control member operationally connected to said energy application head, said control member suitable for controlling said energy application head during treatment of said intervertebral disc;
(b) gaining access to a vertebral column;
(c) epidurally approaching the posterior aspect of said at least one intervertebral disc using said control member to position said energy application head;
(d) evaluating an extent of disc injury and calculating an amount of energy needed to thermally refurbish said at least one intervertebral disc;
(e) applying energy using said disc refurbisher to a posterior aspect of said at least one intervertebral disc while maintaining a safe temperature in said vulnerable tissues near said at least one intervertebral disc;
(f) varying said distance between said energy application region and said tissue protecting region to protect vulnerable tissues associated with said at least one intervertebral disc from said energy;
(g) monitoring an amount of energy delivered and a temperature in said vulnerable tissues near said at least one intervertebral disc;
(h) observing and evaluating an amount of shrinkage and strengthening of said at least one intervertebral disc to determine an intensity and duration of further energy delivery; and
(j) verifying that said shrinkage and strengthening of said at least one intervertebral disc is mechanically successful.

27. The method of claim 26, further comprising the step of applying further energy to other posterior areas of said at least one intervertebral disc to reduce pain.

28. The method of claim 26, said step of applying energy to said posterior aspect of said at least one intervertebral disc further comprising a step selected from the group consisting of:
(a) applying electric current;
(b) applying radio frequency waves;
(c) applying microwaves;
(d) applying infrared waves;
(e) applying visible light waves;
(f) applying ultraviolet waves;
(g) applying ultrasonic sound waves; and
(h) applying conductive thermal energy.

29. The method of claim 26, said step of monitoring an amount of energy delivered further comprising a step selected from the group consisting of:
(a) monitoring using a thermometer;
(b) monitoring using a thermistor;
(c) monitoring using a thyristor;
(d) monitoring using phosphor-coated optic fibers;
(e) monitoring using temperature-sensitive crystals;
(f) monitoring a pressure change in bodily tissue; and
(g) monitoring a volume change in bodily tissue.

30. The method of claim 26, said step of observing and evaluating an amount of shrinkage and strengthening of said at least one intervertebral disc further comprising a step selected from the group consisting of:
(a) observing with unaided vision;
(b) observing with at least one camera;
(c) observing with at least one lens;
(d) observing with at least one mirror;
(e) observing with at least one fiber-optic device;
(f) observing with a mechanical probe; and
(g) observing with a pressure sensor.

* * * * *

UNITED STATES PATENT AND TRADEMARK OFFICE
CERTIFICATE OF CORRECTION

PATENT NO. : 6,673,063 B2
DATED : January 6, 2004
INVENTOR(S) : Darrell C. Brett It is certified that error appears in the above-identified patent and that said Letters Patent is hereby corrected as shown below:

Column 12,
Line 55, delete "instrument" and insert -- insrument; --.

Column 13,
Line 15, after "link;" delete "and".

Column 14,
Line 12, delete "instrument" and insert -- instrument; --.

Column 15,
Lines 19-20, delete "having an energy application head having an energy application head" and insert -- having an energy application head --.

Signed and Sealed this

Twenty-second Day of March, 2005

JON W. DUDAS
*Director of the United States Patent and Trademark Office*